US008098428B2

(12) United States Patent
Kawai et al.

(10) Patent No.: US 8,098,428 B2
(45) Date of Patent: Jan. 17, 2012

(54) CIRCULAR DICHROISM FLUORESCENT MICROSCOPE

(75) Inventors: Tsuyoshi Kawai, Ikoma (JP); Kensuke Kawamura, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 737 days.

(21) Appl. No.: 12/223,446

(22) PCT Filed: Feb. 1, 2007

(86) PCT No.: PCT/JP2007/051734
§ 371 (c)(1),
(2), (4) Date: Jul. 31, 2008

(87) PCT Pub. No.: WO2007/088947
PCT Pub. Date: Aug. 9, 2007

(65) Prior Publication Data
US 2009/0009859 A1    Jan. 8, 2009

(30) Foreign Application Priority Data
Feb. 2, 2006    (JP) ................................ 2006-026030

(51) Int. Cl.
*G02B 21/06*    (2006.01)
(52) U.S. Cl. .......................... 359/386; 359/388; 356/364
(58) Field of Classification Search .................. None
See application file for complete search history.

(56) References Cited

U.S. PATENT DOCUMENTS
3,612,688 A * 10/1971 Liskowitz .................... 356/342
(Continued)

FOREIGN PATENT DOCUMENTS
JP    11-002606    1/1999
(Continued)

OTHER PUBLICATIONS
European Search Report dated Dec. 8, 2010 in corresponding European Application No. 07713762.8.

*Primary Examiner* — Arnel C Lavarias
(74) *Attorney, Agent, or Firm* — Harness, Dickey & Pierce, P.L.C.

(57) ABSTRACT

Example embodiments relate to a circular dichroism fluorescent microscope having a confocal section. In the circular dichroism fluorescent microscope, a circularly polarizing/modulating section converts, into right and left circularly polarized lights, a light beam emitted from a light source. As such, the obtained right and left circularly polarized lights are focused on a sample so that the sample is irradiated with the right and left circularly polarized lights. Then, an optical lens focuses fluorescence emitted from the sample. Further, a wavelength selecting section transmits only fluorescence having a predetermined wavelength. Subsequently, the fluorescence having passed through the wavelength selecting section is detected. Based on fluorescent intensity signals of the fluorescence, a difference between an intensity of the fluorescence emitted from the sample at the time of irradiation with the use of the right circularly polarized light and that with the use of the left circularly polarized light is calculated.

13 Claims, 5 Drawing Sheets

U.S. PATENT DOCUMENTS

| | | |
|---|---|---|
| 2006/0158721 A1 | 7/2006 | Nakata et al. |
| 2006/0192959 A1 | 8/2006 | Manolopoulos et al. |
| 3,817,634 A * | 6/1974 | Barron et al. ............... 356/365 |
| 4,881,818 A * | 11/1989 | Bustamante et al. ......... 356/367 |
| 5,036,204 A * | 7/1991 | Leyden ....................... 250/373 |
| 2003/0058442 A1 | 3/2003 | Garab et al. |
| 2004/0150880 A1 | 8/2004 | Nakata et al. |
| 2005/0200948 A1* | 9/2005 | Trulson et al. ............... 359/391 |
| 2005/0286048 A1 | 12/2005 | Kitagawa |

FOREIGN PATENT DOCUMENTS

| | | |
|---|---|---|
| JP | 11-023466 | 1/1999 |
| JP | 11-051855 | 2/1999 |
| JP | 2003-287685 | 10/2003 |
| JP | 2005-009969 | 1/2005 |
| WO | WO 2004/068119 A1 | 8/2004 |

* cited by examiner

CIRCULAR DICHROISM FLUORESCENT MICROSCOPE

TECHNICAL FIELD

The present invention relates to a circular dichroism fluorescent microscope for observing circular dichroism and, more particularly, relates to a circular dichroism fluorescent microscope for observing a fluorescence detected circular dichroism spectrum or a circularly polarized luminescence dichroism spectrum

BACKGROUND ART

Many of physiologically-active substances have so-called chirality. Examples of such physiologically-active substances are a medical substance, a poisonous substance, and a functional component in a living organism. It is widely known that physiological activities of such substances strongly depend on chirality, that is, high-order structures (conformations, configurations, and the like) of the substances. Thus, it is important in a study of physiologically-active substances to understand chirality of the substances. In this regard, chirality and high-order structures of biomolecules including protein, nucleic acid, and the like, in particular, have been spotlighted in recent years.

These biomolecules are thought to dynamically change their structures in living organisms. For example, an HIV is known to cause AIDS infection by protease that sandwiches and cuts protein of a host. The protease is thought to have a significant change in its conformation when cutting protein. Moreover, a significant change in a high-order structure of prion protein is believed to cause Bovine Spongiform Encephalopathy (BSE).

As is obvious from the above description, analysis of high-order structures of biomolecules such as protein and the like is effective in treatment and diagnosis of diseases. For this reason, techniques for analyzing high-order structures of biomolecules have been developed. Typically known techniques for such analysis are circular dichroism (CD) spectrum analysis, fluorescence detected circular dichroism (FDCD) spectrum analysis, circularly polarized luminescence dichroism (CPL) spectrum analysis, and the like.

For example, Patent Document 1 discloses a technique that relates to the FDCD. Specifically, the Patent Document 1 discloses a method of analyzing chirality which method includes the steps of: introducing a fluorescent functional group to a substance having chirality; exciting the fluorescent functional group by irradiating the group with a right circularly polarized light and a left circularly polarized light and measuring fluorescence intensities that are obtained by excitation with the use of the left and right circularly polarized lights, respectively; and analyzing the chirality of the substance based on difference information between the fluorescence intensities that are obtained by excitation with the use of the right circularly polarized light and excitation with the use of the left circularly polarized light, respectively.

Moreover, Patent Document 2 discloses an apparatus for measuring a circular dichroism fluorescence excitation spectrum which apparatus (i) measures fluorescence intensities obtained by irradiating a sample alternately with the use of a right circularly polarized light and a left circularly polarized light at a predetermined modulation frequency, which circularly polarized lights are for wavelength scanning and homochromatic, and, then, (ii) converts the fluorescence intensities into electrical signals. Patent Document 2 discloses that, in the apparatus, detection sensitivity is improved by independently using, out of the electrical signals, only an alternating-current signal component in synchronization with a frequency for switching between the right and left circularly polarized lights, so as to obtain a circular dichroism fluorescence excitation spectrum.

Furthermore, Patent Document 3 discloses a method and an apparatus for measuring a CPL or an FDCD of a sample by using a laser scanning microscope. For example, FIG. 4 of Patent Document 3 is a diagram schematically illustrating an apparatus for measuring a CPL, while FIG. 9 is a diagram schematically illustrating an apparatus for measuring an FDCD.

(Patent Document 1)
Japanese Unexamined Patent Publication No. 2606/1999 (Tokukai-hei 11-2606) (published on Jan. 6, 1999)
(Patent Document 2)
Japanese Unexamined Patent Publication No. 23466/1999 (Tokukai-hei 11-23466) (published on Jan. 29, 1999)
(Patent Document 3)
USP Application Publication No. 2003/0058442 A1 (published on May 27, 2003)

Chirality of a biomolecule such as protein or the like is believed to depend, to a large extent, on an environment in which the biomolecule exists. For example, it is predicted that protein, nucleic acid, or the like change a conformation thereof, interacting with other protein, a cell membrane, or the like.

However, it is impossible to analyze such a phenomenon in a uniform experimental system in a test tube. Thus, the inventors of the present invention judged that, in analysis of a high-order structure of a biomolecule, it was very important to analyze the structure directly in a living organism (e.g., in a cell or the like). However, all of the aforesaid techniques such as the CD, the FDCD, and the CPL are designed to analyze chirality of substances that exist in uniform solutions. Therefore, these techniques are not suitable for analyzing chirality of substances that exist in non-uniform environments, such as in living organisms, where various substances exist.

Moreover, the technique disclosed in each of the Patent Documents 1 and 2 is not directed to a microscope analysis, and requires a large amount of a sample for analysis. However, generally, only a very small amount of a biomolecule can be prepared. Accordingly, it takes much time and cost to obtain such a large amount of the sample.

Further, according to the technique disclosed in the Patent Document 3, it is highly likely that measurement is not possible at a practical level. Particularly, according to the technique disclosed in the Patent Document 3, it is impossible to analyze a sample that emits light whose circularly polarized light component is small.

In addition, in the technique disclosed in the Patent Document 3, a circularly polarized luminescence dichroism (CPL) spectrum analysis is carried out with the use of a semi-transmissive mirror that serves as means for transmitting an excitation light and reflecting fluorescence light. However, the semi-transmissive mirror (i) lacks wavelength selectivity and (ii) is semi-transmissive. Thus, a loss of light intensity of the incident excitation light occurs. Further, a loss of light intensity of the reflected fluorescence light also occurs. Such losses cause a problem of significant deterioration in measurement accuracy. Moreover, unless the semi-transmissive mirror is arranged exactly at 45 degrees with respect to a light path, distortion occurs. This also results in a problem of significant deterioration in measurement accuracy and stability.

Furthermore, in the technique disclosed in the Patent Document 3, as illustrated in FIG. 4, an iris is disposed near a detecting section. This arrangement causes a problem such that an error occurs in detection of a polarized light component of fluorescence light because the fluorescence light that is emitted from the sample is multi-reflected within a polarization modulating section.

Therefore, it has been strongly desired to develop a technique in which (i) a large amount of a sample is not required for analysis and (ii) a high-order structure of a biomolecule such as protein or the like can be analyzed with high accuracy directly in a living organism. However, research and development of such a technique has not been carried out conventionally. Accordingly, development of the aforesaid technique that contributes to exploitation of novel fields is strongly desired.

The present invention is attained in view of the problem. An object of the present invention is to provide a circular dichroism fluorescent microscope that does not require a large amount of a sample for analysis and that, for example, can analyze, with high accuracy, a high-order structure of a sample including a biomolecule or the like such as protein, directly in a living organism.

DISCLOSURE OF INVENTION

As a result of a diligent study, the inventors of the present invention reached the following findings, and attained the present invention. The inventors found that it is possible to analyze a high-order structure of a sample including a biomolecule (e.g., protein) (i) with the use of a very small amount of the sample and (ii) directly in a living organism, by developing an apparatus that is provided with, in addition to an optical system for detection/excitation and a data processing system in a laser scanning fluorescent microscope, an optical system that carries out fluorescence detected circular dichroism (FDCD) spectrum analysis and circularly polarized luminescence dichroism (CPL) spectrum analysis. The present invention attained based on such a novel finding includes the following inventions.

(1) A circular dichroism fluorescent microscope includes: a light source; circular polarization/modulation means to convert, into a right circularly polarized light and a left circularly polarized light, a light beam emitted from the light source; a first optical lens for focusing the right circularly polarized light and the left circularly polarized light on a sample and irradiating the sample with use of the right circularly polarized light and the left circularly polarized light, the right circularly polarized light and the left circularly polarized light having passed through the circular polarization/modulation means; a second optical lens for focusing fluorescence emitted from the sample; wavelength selection means to transmit only fluorescence having a predetermined wavelength out of the fluorescence focused by the second optical lens; fluorescence measurement means to detect the fluorescence having passed through the wavelength selection means and convert the fluorescence detected into a fluorescence intensity signal; and signal processing means to calculate, based on the fluorescence intensity signal generated by the fluorescence measurement means, a difference between (i) an intensity of fluorescence emitted from the sample at the time when the sample is irradiated with use of the right circularly polarized light and (ii) an intensity of fluorescence emitted from the sample at the time when the sample is irradiated with use of the left circularly polarized light; and confocal means provided between the second optical lens and the wavelength selection means, the confocal means having a fine aperture section.

(2) The circular dichroism fluorescent microscope as set forth in (1), further includes: polarization control means to carry out control so that the circular polarization/modulation means converts, alternately into the right circularly polarized light and the left circularly polarized light at a predetermined modulation frequency, the light beam emitted from the light source; and detection control means to carry out control so that the signal processing means (i) extracts, in synchronization with the modulation frequency, an alternating-current component out of the fluorescence intensity signal generated by the fluorescence measurement means, and then (ii) calculates the difference between (a) the intensity of the fluorescence emitted from the sample at the time when the sample is irradiated with the use of the right circularly polarized light and (b) the intensity of the fluorescence emitted from the sample at the time when the sample is irradiated with the use of the left circularly polarized light.

(3) The circular dichroism fluorescent microscope as set forth in (1), further includes: a third optical lens provided between the second optical lens and the wavelength selection means.

(4) The circular dichroism fluorescent microscope as set forth in (1), wherein: the first optical lens and the second optical lens are of a same optical lens.

(5) The circular dichroism fluorescent microscope as set forth in (1), wherein: a diameter of the fine aperture section is in a range from more than or equal to 10 μm to less than or equal to 100 μm.

(6) A circular dichroism fluorescent microscope includes: a light source; a first optical lens for focusing a light beam emitted from the light source and performing irradiation of the light beam focused; a second optical lens for focusing fluorescence emitted from a sample; a wavelength selecting mirror for reflecting an excitation light from the light source while transmitting the fluorescence emitted from the sample; circular polarization/modulation means to convert, into linearly polarized light components modulated, a right circularly polarized light component and a left circularly polarized light component of the fluorescence having passed through the second optical lens; polarized light block means to block, out of the linearly polarized light components, either a vertical linearly polarized light component or a horizontal linearly polarized light component; wavelength selection means to transmit, out of the circularly polarized light components having passed through the polarized light block means, only light having a predetermined wavelength; fluorescence measurement means to detect the fluorescence that has passed through the wavelength selection means and convert the fluorescence into a florescence intensity signal; signal processing means to calculate, based on the fluorescence intensity signal generated by the fluorescence measurement means, a difference between an intensity of the right circularly polarized light component and an intensity of the left circularly polarized light component of the fluorescence emitted from the sample; and confocal means provided between the wavelength selecting mirror and the fluorescence measurement means, the confocal means having a fine aperture section.

(7) The circular dichroism fluorescent microscope as set forth in (6), wherein: the confocal means is provided between the wavelength selecting mirror and the circular polarization/modulation means.

(8) The circular dichroism fluorescent microscope as set forth in (6), wherein: the confocal means has a function for adjusting the fluorescence that is to reach the circular polarization/modulation means.

(9) The circular dichroism fluorescent microscope as set forth in (6), further includes: polarization control means to carry out control so that the circular polarization/modulation means converts, alternately into the right circularly polarized light and the left circularly polarized light at a predetermined modulation frequency, the fluorescence having passed though the second optical lens; and detection control means to carry out control so that the signal processing means (i) extracts, in synchronization with the modulation frequency, an alternating-current component out of the fluorescence intensity signal generated by the fluorescence measurement means, and then (ii) calculates the difference between the intensity of the right circularly polarized light component and the intensity of the left circularly polarized light component of the fluorescence emitted from the sample.

(10) The circular dichroism fluorescent microscope as set forth in (6), further includes: a third optical lens provided between the polarized light block means and the wavelength selection means.

(11) The circular dichroism fluorescent microscope as set forth in (6), wherein: the first optical lens and the second optical lens are of a same optical lens.

(12) The circular dichroism fluorescent microscope as set forth in (6), wherein: a diameter of the fine aperture section is in a range from more than or equal to 10 µm to less than or equal to 100 µm.

(13) The circular dichroism fluorescent microscope as set forth in (1), further includes; image processing means to form an image of the sample, based on information on the difference between the intensities of the fluorescence, the intensities being calculated by the signal processing means.

(14) The circular dichroism fluorescent microscope as set forth in (6), further includes; image processing means to form an image of the sample, based on information on the difference between the intensities of the fluorescence, the intensities being calculated by the signal processing means.

(15) The circular dichroism fluorescent microscope as set forth in (1) or (6), includes: circular polarization and fluorescence detection wavelength control means (i) to control, by an external signal, the predetermined wavelength of the wavelength selection means and (ii) to control a modulation light wavelength of the circularly polarizing/modulating means.

The circular dichroism fluorescent microscope may be realized by a computer. In this case, the scope of the present invention also encompasses (i) a control program of the circular dichroism fluorescent microscope, which control program causes a computer to operate as the various means above of the circular dichroism fluorescent microscope so as to realize the circular dichroism fluorescent microscope by the computer and (ii) a computer-readable storage medium which records the control program.

For a fuller understanding of the nature and advantages of the invention, reference should be made to the ensuing detailed description taken in conjunction with the accompanying drawings.

REFERENCE NUMERALS

Figure 1:
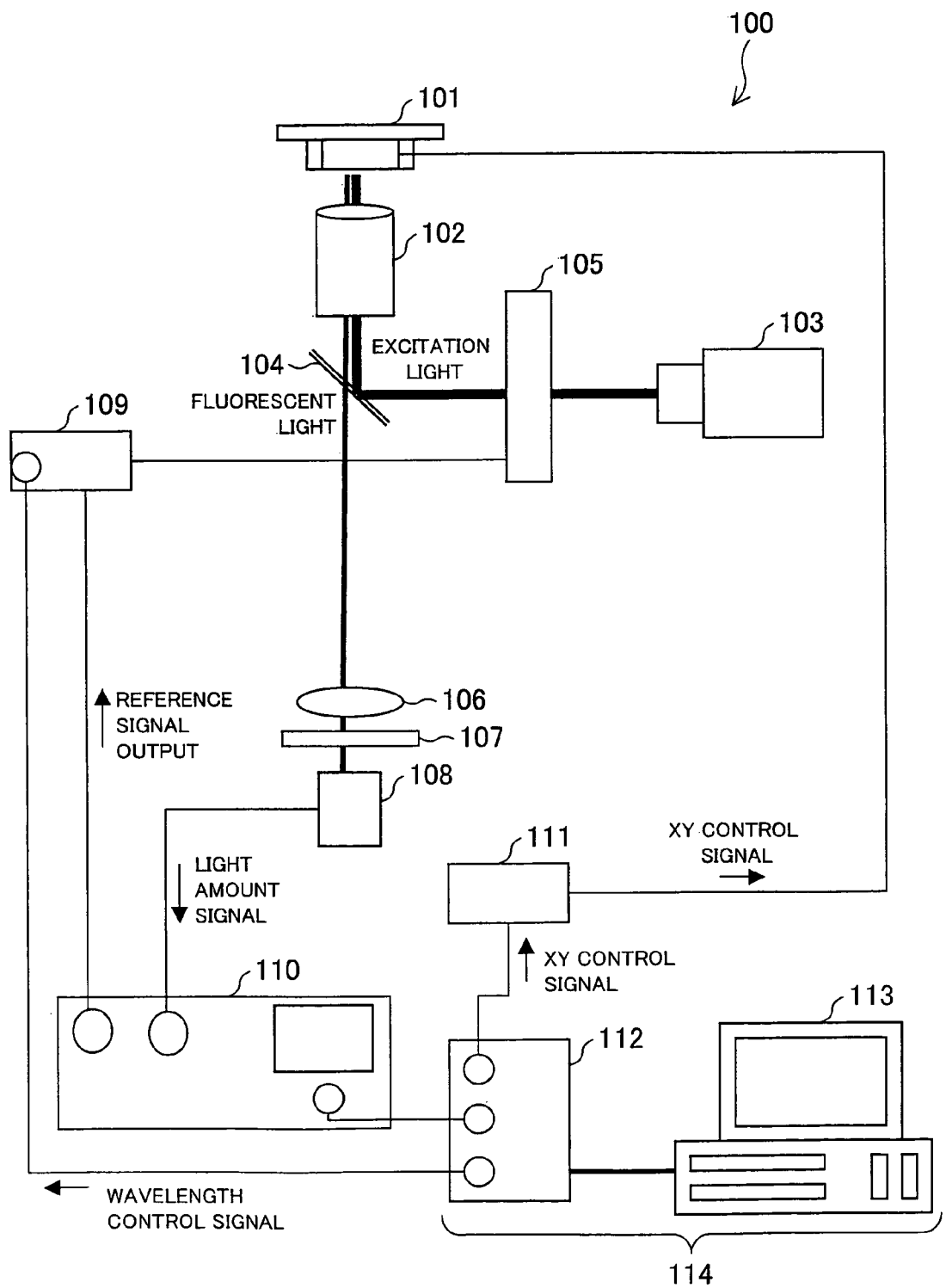
FIG. 1 is a diagram schematically illustrating a configuration of a circular dichroism fluorescent microscope of a Reference Embodiment in accordance with the present invention, which circular dichroism fluorescent microscope carries out two-dimensional analysis of a fluorescence detected circular dichroism spectrum.

100. Circular dichroism fluorescent microscope
100'. Circular dichroism fluorescent microscope
102. Optical lens (first optical lens and second optical lens)
103. Light source
104. Wavelength selecting mirror
105. Circularly polarizing/modulating section (circular polarization/modulation means)
106. Optical lens (third optical lens)
107. Wavelength selecting section (wavelength selection means)
108. Fluorescence measuring section (fluorescence measurement means)
109. Polarization controlling section (polarization control means)
109'. Polarization controlling section (polarization control means)
110. Detection controlling section (detection control means)
114. Signal processing section (signal processing means)
114'. Signal processing section (signal processing means)
115. Confocal section (confocal means)
115'. Confocal section (confocal means)
200. Circular dichroism fluorescent microscope
200'. Circular dichroism fluorescent microscope
205. Circularly polarizing/modulating section (circular polarization/modulation means)
206. Polarized light blocking section (polarized light block means)
210. Detection controlling section (detection control means)
214. Signal processing section (signal processing means)
214'. Signal processing section (signal processing means)
300. Circular dichroism fluorescent microscope

BEST MODE FOR CARRYING OUT THE INVENTION

First, the following description briefly explains the present invention.

As described above, biomolecules such as protein, nucleic acid, and the like have chirality and show properties of circular dichroism such that absorbances of right and left circularly polarized lights are different. Circular dichroism changes significantly, depending on chirality of a molecule and also depending on a direction in which the molecule is measured. Furthermore, it is imagined that chirality of the molecule changes, depending significantly on an environment in which the molecule exists. Therefore, it is expected that the chirality changes by sensitively responding to interaction with a surface of a solid material and a cell membrane or interaction with protein and nucleic acid including DNA. However, analysis of chirality of a molecule in a living organism has not been examined at all. In consideration of exploitation of a novel field, there has been potential demand for development of, for example, an apparatus capable of analyzing chirality of a biomolecule directly in a living organism.

The present invention relates to a technique directed to a microscope capable of carrying out two-dimensional and/or three-dimensional mapping by analyzing, based on circular dichroism, information on chirality of various types of substances. Circular dichroism targeted in the present invention can be broadly classified into two types. Specifically, the circular dichroism is classified into either circularly polarized luminescence dichroism or fluorescence detected circular dichroism. The circularly polarized luminance dichroism can be analyzed by (i) measuring a difference in fluorescence intensity between a case where an excitation light is a + circularly polarized light and a case where the excitation light is a − circularly polarized light and (ii) carrying out mapping. The fluorescence detected circular dichroism can be analyzed by (i) detecting a difference between + and − circularly polarized light components in fluorescence that is generated under linearly polarized light excitation and (ii) carrying out mapping.

A process for analyzing circularly polarized luminescence dichroism can be described more specifically as follows: for example, (1) provide a difference in fluorescence intensity in a case where absorption coefficients are different between (i) a case where an object is irradiated by an excitation light that has been circularly polarized to be a + circularly polarized light and (ii) a case where the object is irradiated with an excitation light that has been circularly polarized to be a − circularly polarized light; (2) for circularly polarizing the excitation light, provide phase-differences of $\pm\lambda/4$ to polarized light components in X direction and Y direction, respectively; (3) for measuring circularly polarized luminescence dichroism, modulate the phase-differences with the use of a sine wave having an amplitude of $\pm\lambda/4$, and then detect synchronized components of the fluorescence intensities by a lock-in amplifier.

On the other hand, a process for analyzing fluorescence detected circular dichroism can be described as follows: for example, (1) detect circularly polarized light components out of fluorescence that is caused by excitation with the use of a linearly polarized light; (2) measure via a polarizer intensities of linearly polarized light components in X and Y directions into which + and − circularly polarized light components are respectively converted at the time when the phase-differences of $\pm\lambda/4$ are given to fluorescence light, the circularly polarized light components changing in accordance with the phase-differences; and (3) for measuring the intensities, modulate periodically the phase-differences, and then detect a synchronized signal by a lock-in amplifier.

It has been impossible in a conventional technique to measure and analyze, simultaneously with identifying a local position where a molecule exists, a state in which chirality of a biomolecule changes in a living cell. The change in chirality occurs in response to interaction between a fluorescent molecule and the biomolecule in the living cell into which a fluorescent coloring matter is introduced so that the cell, protein, and nucleic acid take in the fluorescent coloring matter. On the other hand, with the use of a circular dichroism fluorescent microscope according to the present invention, the analysis of the state becomes possible. Particularly, with the use of a circular dichroism fluorescent microscope according to the present invention, it becomes possible to detect, based on chirality of a molecule, a phenomenon in which the fluorescent coloring matter is taken into a specific part of a cell in response to a specific cell organ or a specific stimulus. Thus, the present invention is a very excellent invention that has a great impact not only on academic fields such as medial science, physiology, and the like, but also on various industries such as a diagnostic/medical instrument industry, an analytical instrument industry, a pharmaceutical industry, a food industry, and the like.

With reference to the drawings, the following raises an example so as to explain in detail (i) Reference Embodiments relating to the present invention that realizes the technological idea described above and (ii) Embodiments according to the present invention.

REFERENCE EMBODIMENT 1

FIG. 1 is a diagram schematically illustrating a configuration of a circular dichroism fluorescent microscope 100 according to the present Reference Embodiment.

A circular dichroism fluorescent microscope 100 is a fluorescent microscope apparatus for two-dimensionally analyzing a fluorescence detected circular dichroism (FDCD) spectrum of a sample. Specifically, the circular dichroism fluorescent microscope 100 includes a sample stage 101, an optical lens 102, a light source 103, a wavelength selecting mirror 104, a circular polarizing modulating section 105, an optical lens 106, a wavelength selecting section 107, a fluorescence measuring section 108, a polarization controlling section 109, a detection controlling section 110, a stage controlling section 111, and a signal processing section 114.

The sample stage 101 is a drive stage that is arranged to be able to move two-dimensionally in XY directions, according to XY control signals from the stage controlling section 111. The sample stage 101 may be provided with a cell holder for holding a cell that contains a sample.

The optical lens 102 serves as a so-called objective lens. That is, the optical lens 102 serves as a first optical lens for focusing, onto a sample, light that has passed through the circularly polarized light modulating section and is reflected by the wavelength selecting mirror 104, and irradiating the sample with the light. The optical lens 102 also serves as a second optical lens for focusing fluorescence that is emitted from the sample. That is, in the present Reference Embodiment, the optical lens 102 serves as the first optical lens and the second optical lens.

An arrangement of the optical lens is not specifically limited. A conventional objective lens, e.g., a 40× magnification objective lens for a fluorescent microscope, can be used as the optical lens. Note that, though the present Reference Embodiment explains, as an example, a configuration in which the optical lens 102 serves as the first optical lens and the second optical lens, the optical lens is not limited to this configuration. Alternatively, the first optical lens and the second optical lens may be provided respectively.

The light source 103 may be a conventional light source as long as the light source can irradiate a sample with a light beam (linearly polarized light). An intensity, a wavelength, and the like of the light beam may be set as appropriate. For example, a laser beam source (405 nm, 5 mW) can be used as the light source 103.

The wavelength selection mirror 104 reflects an excitation light from the light source 103, while transmitting fluorescence from a sample. That is, the wavelength selecting mirror 104 should have an arrangement in which the wavelength selecting mirror 104 (i) reflects the excitation light that is emitted from the light source 103 and transmitted through the circularly polarizing/modulating section 105 while (ii) transmitting the fluorescence that is emitted from the sample. A dichroic mirror, for example, can be used as the wavelength selecting mirror 104. More specifically, the DCM 490 and the like, for example, can be used.

The circularly polarizing/modulating section 105 serves as circular polarization/modulation means that converts, into right and left circularly polarized lights, the light beam that is emitted from the light source 103. More specifically, based on a control signal from the polarization controlling section 109, the circularly polarizing/modulating section 105 converts, alternately into a right circularly polarized light and a left circularly polarized light at a prescribed modulation frequency, the light beam (linearly polarized light) that is emitted from the light source 103. A configuration of the circularly polarizing/modulating section 105 is not specifically limited as long as the circularly polarizing/modulating section 105 has the above function. The circularly polarizing/modulating section 105 may be conventional circular polarization/modulation means, e.g. a PEM modulator such as PM-I/FS 50 manufactured by the HIDNS Instruments, Inc. or the like.

The optical lens 106 focuses the light that has passed through the wavelength selecting mirror 104 on the wavelength selecting section 107. The optical lens 106 serves as a third optical lens that is provided between the wavelength selecting mirror 104 and the wavelength selecting section 107. By providing the third optical lens, it is possible to enhance sensitivity of the microscope.

The wavelength selecting section 107 serves as wavelength selection means that transmits, out of the fluorescence which is focused by the optical lens 102 and then has passed through the wavelength selection mirror 104, only fluorescence that has a predetermined wavelength. A configuration of the wavelength selecting section 107 is not specifically limited. One or a combination of a conventional bandpass filter and a conventional monochrometer or the like may be suitably used.

The fluorescence measuring section 108 serves as fluorescence measurement means that detects the fluorescence having passed through the wavelength selecting section 107 and converts the fluorescence into a fluorescence intensity signal. A conventional light detector can be suitably used for the fluorescence measuring section 108 as long as the light detector has the function as described above. For example, a light detector module H7732-10 manufactured by the Hamamatsu Photonics K. K., or the like, can be suitably used as the fluorescence measuring section 108.

The polarization controlling section 109 serves as polarization control means that controls the circularly polarizing/modulating section 105 so that the circularly polarizing/modulating section 105 converts, alternately into a right circularly polarized light and a left circularly polarized light at a predetermined modulation frequency, the light beam (linearly polarized light) that is emitted from the light source 103. A conventional controlling member can be used suitably as the polarization controlling section 109, as long as the conventional controlling member has a function as described above. For example, a PEM modulator controller or the like may be used as the polarization controlling section 109.

The detection controlling section 110 serves as detection control means. The detection control means carries out control so that the signal processing section 114 extracts, in synchronization with the modulation frequency, an alternating-current component out of the fluorescence intensity signal (electrical signal) that is generated by the fluorescence measuring section 108, and calculates a difference between (i) an intensity of the fluorescence that is emitted from the sample at the time of irradiation with the use of the right circularly polarized light and (ii) an intensity of the fluorescence that is emitted from the sample at the time of irradiation with the use of the left circularly polarized light.

In addition, the detection controlling section 110 receives a light intensity signal from the fluorescence measuring section 108, and outputs a reference signal to the polarization controlling section 109. In other words, the detection controlling section 110 serves as a so-called lock-in amplifier. A conventional controlling member, e.g., a conventional lock-in amplifier, can be suitably used as the detection controlling section 110.

The stage controlling section 111 controls movement of the sample stage 101 in XY directions, based on XY control signals from the signal processing section 114. A configuration of the stage controlling section 111 is not specifically limited. A conventional controlling member can be suitably used as the stage controlling section 111.

The signal processing section 114 serves as signal processing means. The signal processing means calculates, based on the fluorescence intensity signal (electrical signal) that is generated by the fluorescence measurement section 108, a difference between (i) an intensity of the fluorescence that is emitted from the sample at the time of irradiation with the use of the right circularly polarized light and (ii) an intensity of the fluorescence that is emitted from the sample at the time of irradiation with the use of the left circularly polarized light. In other words, the signal processing section 114 calculates a fluorescence detected circular dichroism spectrum of the sample.

Here, the fluorescence detected circular dichroism spectrum records with respect to a wavelength, a difference between (i) an intensity of the fluorescence at the time of excitation with the use of the right circularly polarized light and (ii) an intensity of the fluorescence at the time of excitation with the use of the left circularly polarized light, which fluorescence intensities are measured at the time of irradiating a sample alternately with the use of the right and left circularly polarized lights that are monochromatic.

In addition, the signal processing section 114 serves as circular polarization and fluorescence detection wavelength control means that controls a predetermined wavelength of the wavelength selecting section 107 by an external signal and also controls the modulation light wavelength of the circularly polarizing/modulating section 105.

In the present Reference Embodiment, the signal processing section 114 is a member that controls various control means including the polarization controlling section 109, the detection controlling section 110, and the stage controlling section 111. Specifically, the signal processing section 114 includes an interface 112 that is connected to the various control means above, and an analysis PC 113.

The analysis PC 113 is arranged to control, through the interface 112, the various control means including the polarization controlling section 109, the detection controlling section 110, and the stage controlling section 111. Specifically, the analysis PC 113 transmits, through the interface 112, (i) a wavelength control signal to the polarization controlling section 109 and (ii) XY control signals to the stage controlling section 111. An example of such an interface 112 is a GP-IB interface or the like.

Furthermore, the analysis PC 113 may be arranged to serve as image processing means that forms an image of the sample, based on information on the difference of fluorescence intensities, which difference has been calculated. The analysis PC 113 also serves as means that performs imaging and mapping based on chirality information of the sample. A mechanism for the imaging and mapping is not specifically limited. Conventional means, mechanism, or software may be used. A preferable example of the mechanism is software for carrying out imaging/mapping by using data from a laser scanning fluorescent microscope. An arrangement or the like of the signal processing section 114 is not specifically limited as long as the image processing section 114 includes at least the functions described above. Therefore, except a point specified particularly, a conventional operation device (hardware) or software can be suitably used as the signal processing section 114.

The following explains a specific example of signal processing in the mechanism of the image mapping. Note that the following explains a process that is carried out after the difference of the fluorescence intensities is calculated. In the example described below, it is also possible to transmit, from a detection controlling section (lock-in amplifier) to a signal controlling section, a direct-current component as well as an alternating-current component.

More specifically, a signal includes an alternating-current component and a direct-current component. The alternating-current component is proportional to chirality and the number of molecules (density) while the direct-current component is proportional to the number of molecules. Thus, it is possible to analyze data more accurately by mapping a g value (chirality anisotropy parameter) obtained by the following mathematical formula:

$$g = I_+ - I_- / (\tfrac{1}{2}(I_+ - I_-)) = 2 \text{ alternating-current components/a direct-current component.}$$

Next, the following explains an operation that is performed at the time when the circular dichroism fluorescent microscope 100 analyzes a fluorescence detected circular dichroism spectrum of a sample.

First, the circularly polarizing/modulating section 105 is irradiated with the use of a linearly polarized laser beam from the light source 103. The circularly polarizing/modulating section 105 then converts the linearly polarized laser beam into right and left circularly polarized excitation lights. The circularly polarized excitation lights thus obtained enters the optical lens 102 via the wavelength selecting mirror 104. Subsequently, the circularly polarized excitation lights are focused on a sample on the sample stage 101, and the sample is irradiated with the use of the focused circularly polarized excitation lights. The sample is fixed on the sample stage 101, and the signal processing section 114 (specifically, the analysis PC 113) controls, through the stage controlling section 111, a position of the sample.

The circularly polarizing/modulating section 105 is arranged to provide a phase-difference to the excitation light (through the polarization controlling section 109). The phase-difference has (i) a frequency ω that is defined by a reference signal from the detection controlling section 110 and (ii) an amplitude ±λ/4, where λ indicates a wavelength of the excitation light (circularly polarized laser beam). λ is provided from the analysis PC 113 of the signal processing section 114 to the interface 112, and then provided as a wavelength control signal, to the circularly polarizing/modulating section 105 through the polarization controlling section 109. As a result, the circularly polarizing/modulating section 105 modulates, alternately to a right circularly polarized light and a left circularly polarized light, the light beam (linearly polarized light) that is emitted from the light source 103. The modulation is performed at a predetermined modulation frequency.

Then, the circularly polarized excitation light is focused so as to irradiate the sample with the light. Consequently, fluorescence is emitted from the sample. The fluorescence that is emitted from the sample is focused by the optical lens 102 and passes, as a parallel light, through the wavelength selecting mirror 104, the optical lens 106, and the wavelength selecting section 107. As a result, the fluorescence is converted into a fluorescence intensity signal (an electrical signal) by the fluorescence measuring section 108. Ultimately, the fluorescence intensity signal is outputted, as a light amount signal, to the detection controlling section 110.

In the above operation, in a case where, for example, an absorbance of the sample with respect to the excitation light is high with respect to the right circularly polarized light (for convenience, referred to as "+" circularly polarized light) and an absorbance of the sample with respect to the excitation light is low with respect to the left circularly polarized light (for convenience, referred to as "−" circularly polarized light), a strong fluorescence signal is detected at the time when the circularly polarizing/modulating section 105 provides a phase-difference of +λ/4 and a weak fluorescence signal is detected at the time when the circularly polarizing/modulating section 105 provides a phase-difference of −λ/4. Therefore, the electrical signal (light amount signal) from the fluorescence measuring section 108 is modulated by the detection controlling section 110 at a frequency of ω. Data of signal components thus modulated is transmitted through the interface 112 to the analysis PC 113.

Then, the analysis PC 113 calculates a difference between (i) an intensity of fluorescence that is emitted from the sample at the time of irradiation with the use of the right circularly polarized light and (ii) an intensity of fluorescence that is emitted from the sample at the time of irradiation with the use of the left circularly polarized light, and analyzes a fluorescence detected circular dichroism spectrum of the sample. Besides, the analysis PC 113 forms an image of the fluorescence detected circular dichroism spectrum according to positional information of the sample stage 101, so as to carry out mapping.

A sample to be analyzed by the circular dichroism fluorescent microscope 100 is not particularly limited, as long as it is desired to analyze chirality, a high-order structure, a conformation, and the like of the sample. Accordingly, various samples may be targets of the analysis. Particularly, it is preferable that the circular dichroism fluorescent microscope 100 is used to analyze a high-order structure and chirality information of a biomolecule such as protein and nucleic acid in a living organism.

It is preferable that a fluorescent substance is introduced to a sample to be analyzed so as to prepare a sample that emits fluorescence by absorbing an excitation light. An example of such a fluorescent substance is a fluorescent functional group. One example of a method for preparing the sample is a method of converting a sample to a fluorescent material by introducing the fluorescent functional group with the use of chemical means. A fluorescent functional group is not specifically limited. A functional group including naphthalene ring, anthracene ring, pyrene ring, perylene ring, coronene ring, porphyrin ring, or the like is preferable for a subsequent analysis. This is because: such a group mentioned above has a high fluorescence intensity; the group is highly symmetrical; and an electron state, directions of transition moments of absorption and fluorescence, and the like of the group are sufficiently studied. Note that a method of converting a sample into a fluorescent material is not limited to the method above, but the sample can be converted into a fluorescent material by using various substances and methods in accordance with the object of the preset invention.

With the use of the circular dichroism fluorescent microscope 100 described above, it is possible to analyze a fluorescence detected circular dichroism spectrum even in a case where an absolute amount of a sample is small. This is advantageous in that a large amount of a sample is not required. Besides, with the use of the circular dichroism fluorescent microscope, it is possible to analyze, directly in a living cell (e.g., in a cell kept alive), chirality information, a high-order structure, a conformation, and the like of a biomolecule such as protein and nucleic acid that are present in the cell.

Besides, it is also possible to analyze a sample, such as blood and body fluid (including saliva), which sample has a light scattering property. Because it is hard to analyze a sample having a light scattering property with the use of an ordinary spectrum analysis apparatus, an effect of the present invention is significantly advantageous. Because a body fluid such as blood, saliva, and the like generally scatters light (because a body fluid is cloudy), a preliminary treatment of the body fluid is necessary before analysis with the use of a spectrometer. On the other hand, because a circular dichroism fluorescent microscope of the present Reference Embodiment is capable of directly analyzing a light scattering sample, the Reference Embodiment has a specific effect such that the light scattering sample does not require a preliminary treatment for analysis.

Embodiment 1

Reference Embodiment 1 explains one embodiment of a circular dichroism fluorescent microscope for two-dimensionally analyzing a fluorescence detected circular dichroism spectrum. The present embodiment explains one embodiment of a circular dichroism fluorescent microscope that three-dimensionally analyzes a fluorescence detected circular dichroism spectrum by having a confocal microscope configuration. For convenience of an explanation, members having the same functions as those described in Reference Embodiment 1 are given the same reference numerals and the explanations thereof are omitted. The present embodiment explains a difference between the present embodiment and Reference Embodiment 1.

Figure 2:
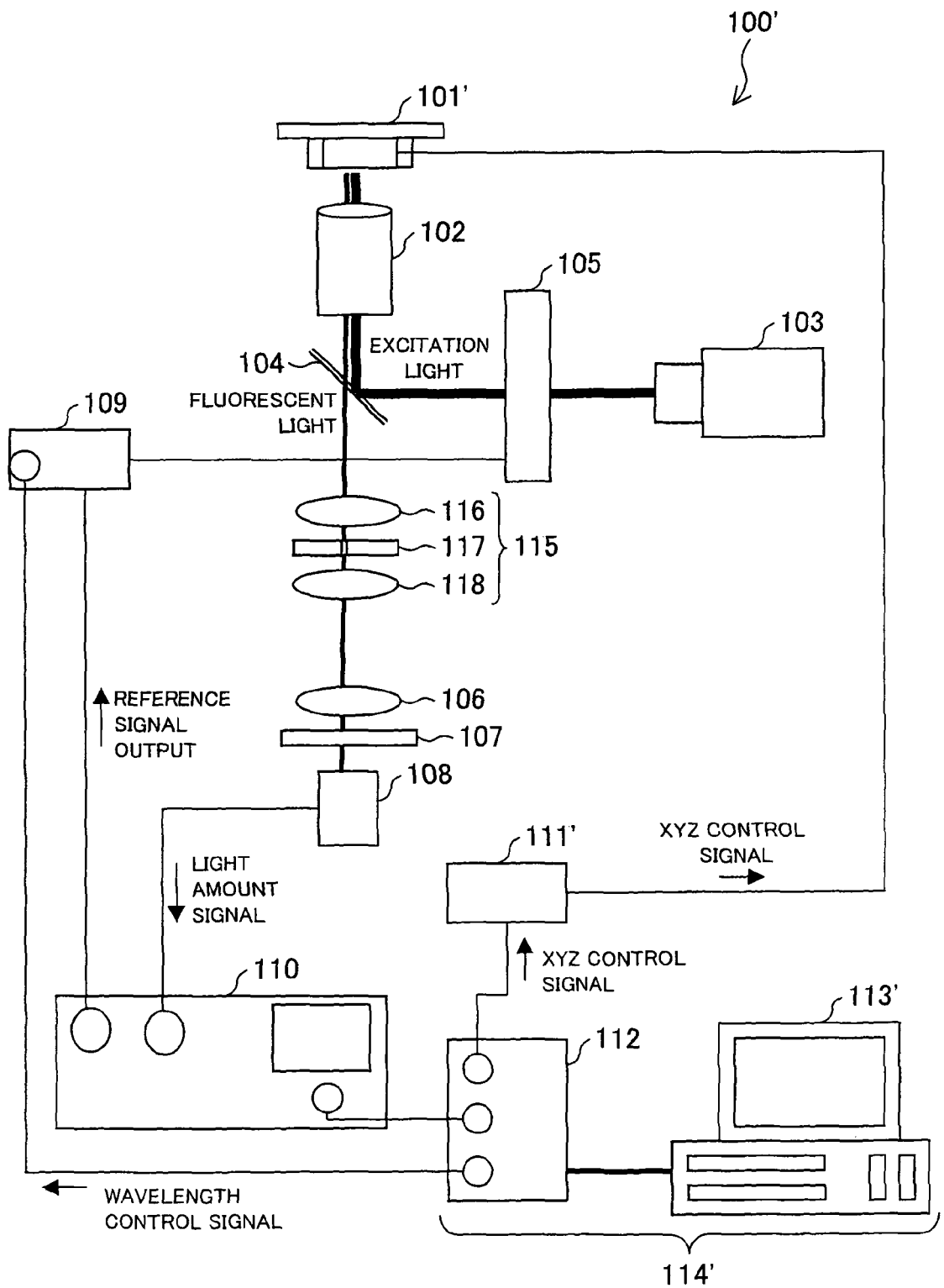
FIG. 2 is a diagram schematically illustrating a configuration of a circular dichroism fluorescent microscope of an embodiment in accordance with the present invention, which circularly dichroism fluorescent microscope carries out three-dimensional analysis of a fluorescence detected circular dichroism spectrum.

FIG. 2 is a diagram schematically illustrating a configuration of a circular dichroism fluorescent microscope 100' in accordance with the present invention.

The circular dichroism fluorescent microscope 100' is a fluorescent microscope for three-dimensionally analyzing a fluorescence detected circular dichroism spectrum of a sample. The circular dichroism fluorescent microscope 100' is different from a circular dichroism fluorescent microscope of Reference Embodiment 1 the most significantly in that a mechanism of a confocal microscope is adopted. Specifically, the circular dichroism fluorescent microscope 100 includes a sample stage 101', an optical lens 102, a light source 103, a wavelength selecting mirror 104, a circularly polarizing/modulating section 105, an optical lens 106, a wavelength selecting section 107, a fluorescence measuring section 108, a polarization controlling section 109, a detection controlling section 110, a stage controlling section 111', a signal processing section 114', and a confocal section 115.

The sample stage 101' is a three-dimensional drive stage capable of, in addition to the functions of the sample stage in accordance with Reference Embodiment 1, moves in a Z axis direction. Accordingly, the stage controlling section 111' outputs XYZ signals so as to control the movement of the sample stage 101'. Instead of the sample stage 101', the optical lens 102 may be arranged so as to move in the Z axis direction (a direction in which the sample stage 101' and the optical lens 102 come closer to each other and/or move away from each other). As a control system and other configurations in the arrangement above, conventional technique, system, or the like can be suitably used.

The signal processing section 114' includes an interface 112 and an analysis PC 113' for a three-dimensional analysis. The analysis PC 113' three-dimensionally analyzes a fluorescence detected circular dichroism spectrum based on data from a confocal microscope. A technique and a mechanism of processing three-dimensional data are not specifically limited, and conventional software for analyzing three-dimensional data or the like can be used suitably. Note that a principle of a technique for analyzing a fluorescence detected circular dichroism spectrum in the present embodiment is the same as that of Reference Embodiment 1. Moreover, the analysis PC 113' may be arranged so as to be able to carry out an imaging/mapping process.

Besides, the signal processing section 114' may be arranged in a same manner as the signal processing section 114 so as to (i) control a predetermined wavelength of the wavelength selecting section 107 by an external signal and (ii) serve as circular polarization and fluorescence detection wavelength control means for controlling a modulation light wavelength of the circularly polarizing/modulating section 105.

The confocal section 115 is provided between the wavelength selecting mirror 104 and the wavelength selecting section 107 (more specifically, the optical lens 106). The confocal section 115 includes an optical lens 116, a pinhole plate 117 having a fine aperture section, and an optical lens 118. The optical lens 116 is a lens for focusing light on the fine aperture section of the pinhole plate 117. An optical lens 118 is a lens for focusing the light that has passed through the fine aperture section on the optical lens 106. Such a confocal section 115 may include only a pinhole plate that has a fine aperture section. However, it is more preferable that the confocal section 115 is a confocal unit (confocal scanner) that is constituted by a pinhole plate and an optical system, as in the present embodiment. The confocal section 115 can employ a conventional confocal unit. A specific arrangement of the confocal section 115 may be modified as appropriate according to an object of the present invention.

An operation of the circular dichroism fluorescent microscope 100' is substantially the same as an operation of the circular dichroism fluorescent microscope 100 of Reference Embodiment 1, except in that fluorescence that has passed through the wavelength selecting mirror 104 passes through the confocal section 115 before arrival at the optical lens 106. Thus, the detailed explanation of the operation is omitted. In the arrangement described above, out of fluorescence that is emitted from a sample, only light focused on the fine aperture section passes through the confocal section 115 while other light is blocked. Thus, the fluorescence detecting section 108 can obtain a confocal image from the fluorescence that is emitted from the sample. Then, the signal processing section 114' three-dimensionally analyzes a fluorescence detected circular dichroism spectrum based on data of this confocal image.

Specifically, it is preferable that a diameter of the fine aperture section of the pinhole plate 117 is in a range from 10 μm to 100 μm. It is more preferable that the diameter is in a range from 30 μm to 50 μm. If the diameter of the fine aperture section falls within the ranges above, the fluorescence from the sample can be reliably adjusted. Thus, it becomes possible to obtain a confocal image of a higher accuracy.

In addition to an effect described in Reference Embodiment 1, the arrangement above makes it possible to three-dimensionally analyze chirality information, a high-order structure, a conformation, and the like of, for example, a biomolecule such as protein and nucleic acid in a cell. Moreover, it is clear that imaging/mapping can be performed. A specific example of signal processing in the mechanism of image mapping is the same as that in Reference Embodiment 1, and, thus, the explanation thereof is omitted.

Reference Embodiment 2

Each of Reference Embodiment 1 and Embodiment 1 explains one embodiment of a circular dichroism fluorescent microscope for two-dimensionally or three-dimensionally analyzing a fluorescence detected circular dichroism spectrum. The present embodiment explains one embodiment of a circular dichroism fluorescent microscope that can two-dimensionally analyze a circularly polarized luminescence dichroism (CPL) spectrum analysis. For convenience of an explanation, members having the same functions as those described in Reference Embodiment 1 and/or Embodiment 1 are given the same reference numerals, and the explanations thereof are omitted. The present embodiment explains a difference between Reference Embodiment 2 and the above Reference embodiment 1 and/or Embodiment 1.

Figure 3:
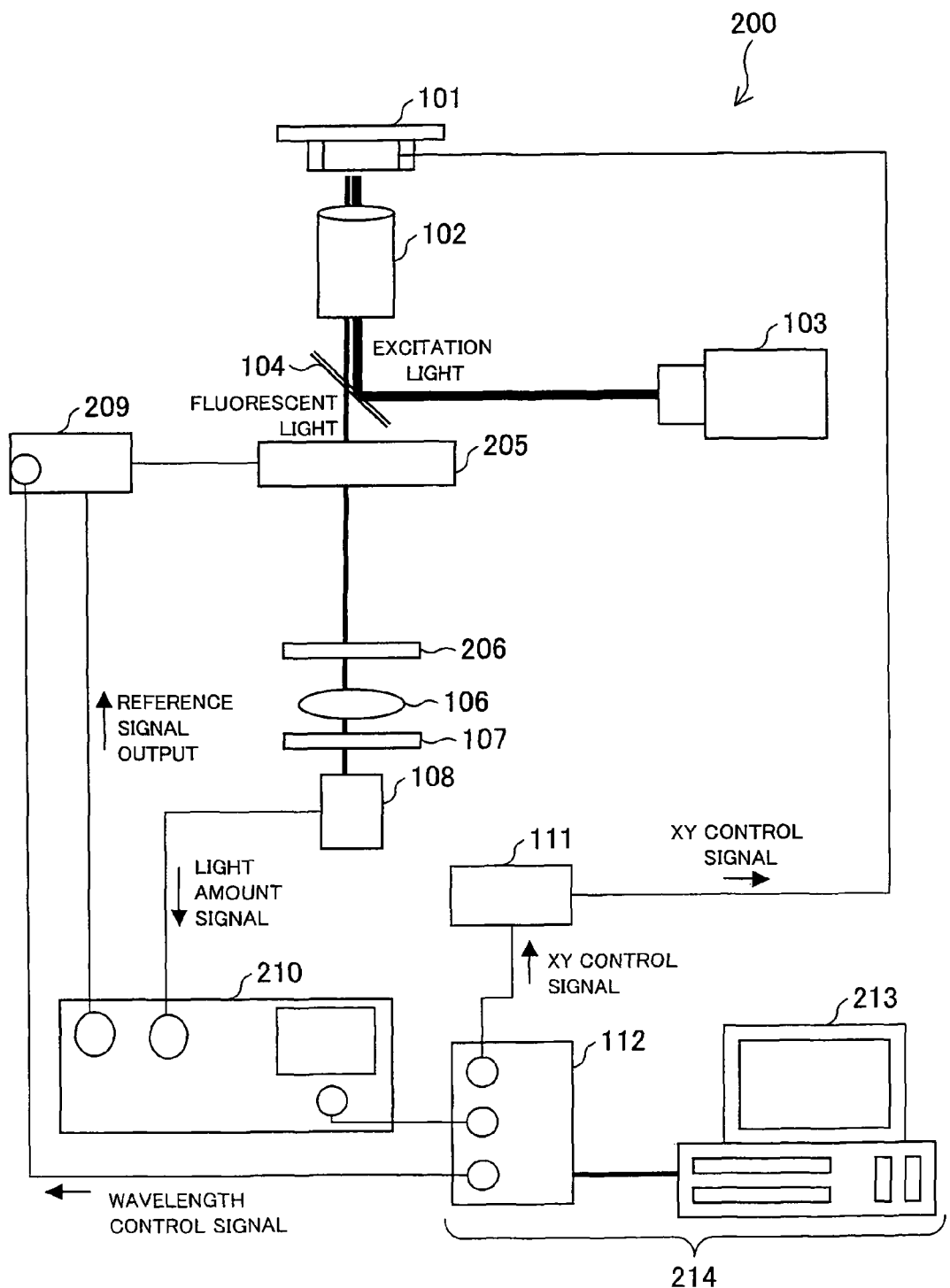
FIG. 3 is a diagram schematically illustrating a configuration of a circular dichroism fluorescent microscope of a Reference Embodiment in accordance with the present invention, which circular dichroism fluorescent microscope carries out two-dimensional analysis of a circularly polarized luminescence dichroism spectrum.

FIG. 3 is a diagram schematically illustrating a configuration of a circular dichroism fluorescent microscope 200 in accordance with a present Reference Embodiment. The circular dichroism fluorescent microscope 200 is a fluorescent microscope for two-dimensionally analyzing a circularly polarized luminescence dichroism (CPL) spectrum analysis of a sample.

Specifically, the circular dichroism fluorescent microscope 200 includes a sample stage 101, an optical lens 102, a light source 103, a wavelength selecting mirror 104, a circularly polarizing/modulating section 205, a polarization blocking section 206, an optical lens 106, a wavelength selecting section 107, a fluorescence measuring section 108, a polarization controlling section 209, a detection controlling section 210, a stage controlling section 111, and a signal processing section 214.

The circularly polarizing/modulating section 205 serves as circular polarization/modulation means for converting, into modulated linearly polarized light components, a right circularly polarized light component and a left circularly polarized light component of fluorescence that has passed through the optical lens 102. More specifically, the circularly polarizing/modulating section 205 is controlled by the polarization controlling section 209 so as to process at a predetermined modulation frequency the fluorescence (circularly polarized light components) that has passed through the optical lens 102 and convert the fluorescence into a linearly polarized light component. A configuration of the circularly polarizing/modulating section 205 is not specifically limited as long as the circularly polarizing/modulating section 205 functions as described above. A conventional circular polarization/modulation means can be used as the circularly polarizing/modulating section 205. An example of such conventional circular polarization/modulation means is a PEM modulator such as PM-1/FS 50 that is manufactured by the HIDNS Instruments, Inc. or the like.

The polarization blocking section 206 serves as polarized light block means for blocking, out of the linearly polarized light components that are modulated by the circularly polarizing/modulating section 205, either a vertical linearly polarized light component or a horizontal linearly polarized light component. An example of such a polarization blocking section 206 is, a conventional polarizer.

The polarization controlling section 209 serves as polarization control means for carrying out control so that the circularly polarizing/modulating section 205 converts fluorescence into a linearly polarized light component by processing, at a predetermined modulation frequency, the fluorescence (circularly polarized light components) that has passed through the optical lens 102. A conventional control member can be suitably used for such a polarization controlling section 209, as long as the control member functions as described above. An example of such a control member is a PEM modulator controller or the like.

The detection controlling section 210 serves as detection control means for carrying out control so that the signal processing section 214 (i) extracts in synchronization with the modulation frequency an alternating-current component out of a fluorescence intensity signal (electrical signal) that is generated by the fluorescence measuring section 108, and then (ii) calculates a difference between an intensity of a right circularly polarized light component and an intensity of a left circularly polarized light component of the fluorescence that is emitted from a sample. Besides, the detection controlling section 210 receives a light amount signal from the fluorescence measuring section 108 and outputs a reference signal to the polarization controlling section 209. In other words, the detection controlling section 210 serves as a so-called lock-in amplifier. A conventional control member can be used as the controlling section. An example of the control section is a conventional lock-in amplifier.

The signal processing section 214 serves as signal processing means for calculating, based on a fluorescence intensity signal (electrical signal) that is generated by the fluorescence measuring section 108, a difference between an intensity of the right circularly polarized light component of fluorescence that is emitted from the sample and the left circularly polarized light component of the fluorescence. In other words, the signal processing section 214 calculates a circularly polarized luminescence dichroism spectrum of the sample.

Here, a circularly polarized luminescence dichroism spectrum records, with respect to a wavelength, a difference between an intensity of a right circularly polarized light component of the fluorescence and a left circularly polarized light component of the fluorescence which intensities are obtained by measuring a degree of polarization of the fluorescence that is emitted from a sample at the time when the sample is irradiated with the use of a linearly polarized light.

In the present Reference Embodiment, the signal processing section 214 is a member for controlling various control means such as the polarization controlling section 209, the detection controlling section 210, and the stage controlling section 111. Specifically, the signal processing section 214 includes (i) an interface 112 that is connected to each of the various control means, and (ii) an analysis PC 213.

The analysis PC 213 is arranged so as to control, through the interface 112, the various control means such as the polarization controlling section 209, the detection controlling section 210, and the stage controlling section 111. Specifically, the analysis PC 213 transmits, through the interface 112, a wavelength control signal to the polarization controlling section 209 and XY control signals to the stage controlling section 111. An example of such an interface 112 is a GP-IB interface or the like.

Moreover, the signal processing section 214 may be arranged so as to serve as circular polarization and fluorescence detection wavelength control means for (i) controlling a predetermined wavelength of the wavelength selecting section 107 by an external signal and (ii) controlling a modulation light wavelength of the circularly polarizing/modulating section 205 in accordance with thus set wavelength of the wavelength selecting section 107.

Further, the analysis PC 213 may also be arranged so as to serve as image processing means for forming an image of the sample based on information on a difference of fluorescence intensities that are calculated by the signal processing section 214. This image processing means is means for performing imaging and mapping of chirality information of the sample. A mechanism for such imaging/mapping is not specifically limited, and conventional means, mechanism, and software can be used as the mechanism. An example of the mechanism is software that carries out imaging and mapping by using data from a laser scanning fluorescent microscope or the like. As is clear from the above, an arrangement of the signal processing section 214 is not specifically limited, as long as the signal processing section 214 has at least the functions described above. A conventional arithmetic device (hardware) or software can be used suitably, except in the point specified particularly.

A specific example of signal processing in the image mapping mechanism is the same as that of the Reference Embodiment 1. Therefore, the explanation thereof is omitted.

Next, the following explains an operation in which a circular dichroism fluorescent microscope 200 analyzes a circularly polarized luminescence dichroism spectrum of a sample.

First, a linearly polarized laser beam is emitted from the light source 103 and the optical lens. 102 is irradiated with the use of the linearly polarized laser beam via the wavelength selecting mirror 104. The optical lens 102 focuses the linearly polarized laser beam on a sample on a sample stage 101. The sample is fixed on the sample stage 101, and a position of the sample is controlled, through the stage controlling section 111, by the signal processing section 214 (specifically, by the analysis PC 213).

Fluorescence is emitted from the sample in response to the focusing of the linearly polarized laser beam (excitation light) on the sample and irradiation of the sample with the use of the linearly polarized laser beam. The fluorescence that is emitted from the sample is focused by the optical lens 102 and passes through, as a parallel light, the wavelength selecting mirror 104. Then, the fluorescence enters the circularly polarizing/modulating section 205. The circularly polarizing/modulating section 205 is arranged so as to provide (through a polarization controlling section 209) the fluorescence light with a phase-difference of (i) a frequency ω that is defined by a reference signal from the detection controlling section 210 and (ii) an amplitude ±λ/4, where λ is a measured wavelength. The measured wavelength that has been provided from the analysis PC 213 via the interface 112 is provided as a wavelength control signal via the polarization controlling section 209, in accordance with maximum of fluorescence.

In a case where the circularly polarizing/modulating section 205 provides a phase-difference of +λ/4 to the fluorescence light and converts a right circularly polarized light into a linearly polarized light (for convenience, a right circularly polarized light component in this case is referred to as a "+" component), the polarized light blocking section 206 blocks a left circularly polarized light component (for convenience, referred to as a "−" component) out of the circularly polarized light components of the fluorescence that has passed through the circularly polarizing/modulating section 205. On the other hand, the right circularly polarized light component passes through the polarization blocking section 206, the optical lens 106, and the wavelength selecting section 107. Then, the right circularly polarized light component is converted into a fluorescence intensity signal (electrical signal) by the fluorescence measuring section 108. Subsequently, the fluorescence intensity signal is outputted, as a light amount signal, to the detection controlling section 210.

In addition, in a case where the circularly polarizing/modulating section 205 provides a phase-difference of −λ/4 to the fluorescence light so as to convert the left circularly polarized light into a linearly polarized light (for convenience, a left circularly polarized light component in this case is referred to as a "+" component), the polarized light blocking section 206 cuts a right circularly polarized light component (for convenience, referred to as a "−" component) out of the circularly polarized light components of the fluorescence light that has passed through the circularly polarizing/modulating section 205. On the other hand, the left circularly polarized light component passes through the polarization blocking section 206, the optical lens 106, and the wavelength selecting section 107. Then, the left circularly polarized light component is converted into a fluorescence intensity signal (electrical signal) by the fluorescence measuring section 108. Subsequently, the fluorescence intensity signal is outputted, as a light amount signal, to the detection controlling section 210.

In the operation above, in a case where the right and left circularly polarized light components are equivalent, a constant electrical signal is obtained regardless of the phase modulation by the circularly polarizing/modulating section 205. However, in a case where a right circularly polarized light component is greater, (i) a strong electrical signal is obtained by a phase-difference of +λ/4 that is provided by the circularly polarizing/modulating section 205 and (ii) a weaker electrical signal is obtained by a phase-difference of −λ/4 that is provided by the circularly polarizing/modulating section 205. This means that, in such a case, the signal that is outputted from the fluorescence measuring section 108 is modulated at the frequency ω.

The modulation signal component is detected, as a light amount signal, by the detection controlling section 210, and then data of the light amount signal is transmitted to the analysis PC 213 through the interface 112 of the signal processing section 214. Subsequently, the analysis PC 213 analyzes the circularly polarized luminescence dichroism spectrum. In conjunction with this analysis, imaging and mapping of the circularly polarized luminescence dichroism spectrum may be carried out.

The circular dichroism fluorescent microscope 200 firstly makes it possible to analyze a circularly polarized luminescence dichroism spectrum even when an absolute amount of a sample is small. This leads to a merit such that a large amount of the sample is not necessary. Moreover, the circular dichroism fluorescent microscope 200 makes it possible to analyze chirality information, a high-order structure, a conformation, and the like in a cell, for example, with respect to a biomolecule such as protein and nucleic acid present in the cell. Furthermore, the circular dichroism fluorescent microscope 200 makes it possible to analyze a light scattering sample such as blood, body fluid (including saliva), and the like.

Embodiment 2

Reference embodiment 2 explains one embodiment of the circular dichroism fluorescent microscope for analyzing two-dimensionally a circularly polarized luminescence dichroism spectrum. The present embodiment explains one embodiment of a circular dichroism fluorescent microscope that three-dimensionally analyzes a circularly polarized luminescence dichroism spectrum by having a confocal microscope configuration. For convenience of an explanation, members having the same functions as those described in Reference Embodiments 1 and 2 and Embodiment 1 are given the same reference numerals, and the explanations thereof are omitted. The present embodiment explains how the present embodiment is different from Reference Embodiments 1 and 2 and Embodiment 1.

Figure 4:
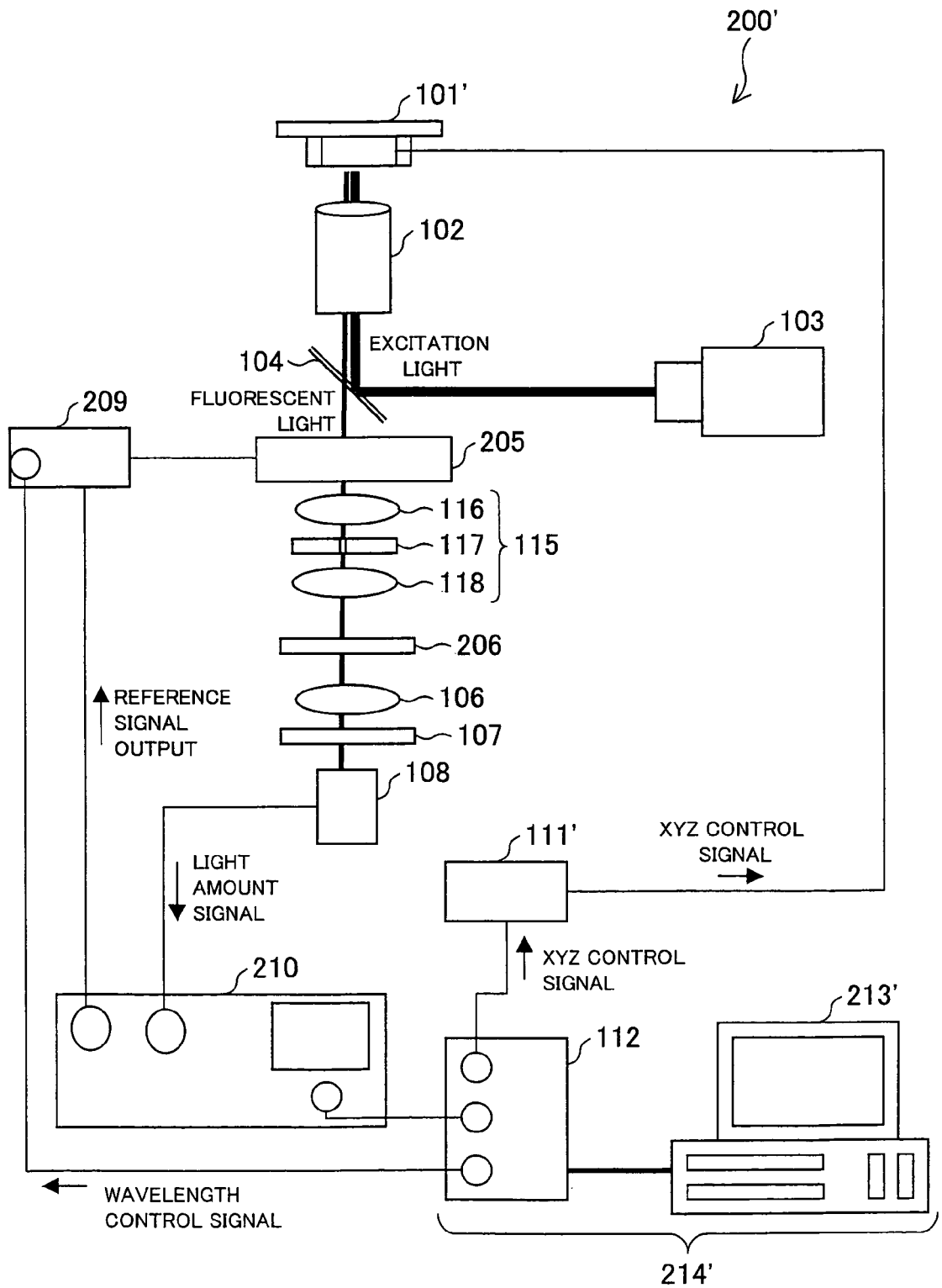
FIG. 4 is a diagram schematically illustrating a configuration of a circular dichroism fluorescent microscope of an embodiment in accordance with the present invention, which circular dichroism fluorescent microscope carries out three-dimensional analysis of a circularly polarized luminescence dichroism spectrum.

FIG. 4 is a diagram schematically illustrating a configuration of a circular dichroism fluorescent microscope 200' in accordance with the present embodiment. The circular dichroism fluorescent microscope 200' is a fluorescent microscope for three-dimensionally analyzing a circularly polarized luminescence dichroism (CPL) spectrum analysis of a sample by having a confocal configuration.

Specifically, the circular dichroism fluorescent microscope 200' includes a sample stage 101', an optical lens 102, a light source 103, a wavelength selecting mirror 104, a circularly polarizing/modulating section 205, a polarization blocking section 206, an optical lens 106, a wavelength selecting section 107, a fluorescence measuring section 108, a polarization controlling section 209, a detection controlling section 210, a stage controlling section 111', a signal processing section 214', and a confocal section 115.

The signal processing section 214' includes an interface 112 and an analysis PC 213' for a three-dimensional analysis. The analysis PC 213' three-dimensionally analyzes a circularly polarized luminescence dichroism spectrum based on data from a confocal microscope. A method and a mechanism for processing three-dimensional data are not specifically limited. Conventional software for analyzing three-dimensional data or the like can be used suitably. A principle of the method for analyzing a circularly polarized luminescence dichroism spectrum is the same as that in Reference Embodiment 2. Moreover, the analysis PC 213' may be arranged so as to be able to carry out an imaging/mapping process. A specific example of signal processing in an imaging/mapping mechanism is the same as that in Reference Embodiment 1, and thus the explanation thereof is omitted.

Furthermore, the signal processing section 214' may be arranged in the same manner as the signal processing section 214 so as to serve as circular polarization and fluorescence detection wavelength control means that (i) controls, by an external signal, a predetermined wavelength of the wavelength selecting section 107 and (ii) controls a modulation light wavelength of the circularly polarizing/modulating section 205.

An operation of the circular dichroism fluorescent microscope 200' is substantially the same as the operation of the circular dichroism fluorescent microscope 200 in accordance with Reference Embodiment 2, except in that fluorescence that has passed through the circularly polarizing/modulating section 205 passes through the confocal section 115 and then reaches the polarization blocking section 206. Therefore, a detailed explanation of the operation of the circular dichroism fluorescent microscope 200' is omitted. In the above arrangement, only light that focuses on a fine aperture section, out of fluorescence that is emitted from a sample, passes through the confocal section 115 while other light is blocked. Therefore, it is possible to obtain, by the fluorescence detecting section 108, a confocal image from the fluorescence that is emitted form the sample. Then, the signal processing section 214' three-dimensionally analyzes a circularly polarized luminescence dichroism spectrum, based on data of thus obtained confocal image.

According to the above arrangement, in addition to an effect described in Reference Embodiment 2, it becomes possible to three-dimensionally analyze chirality information, a high-order structure, a conformation, and the like in a living organism, with respect to a biomolecule, such as protein and nucleic acid, present in the cell. Further, clearly, an imaging/mapping process can be performed.

In the present embodiment, the confocal section 115 is provided between the circularly polarizing/modulating section 205 and the polarization blocking section 206. Alternatively, the confocal section 115 may be arranged so as to be provided between the polarization blocking section 206 and the optical lens 106. A position of the confocal section 115 is not specifically limited to these arrangements, and may be varied in many ways within the scope in which the object of the present invention can be attained.

Embodiment 3

Embodiment 2 above explains one embodiment of a circular dichroism fluorescent microscope for analyzing three-dimensionally a circularly polarized luminescence dichroism spectrum. The present embodiment explains one embodiment of a circular dichroism fluorescent microscope (i) that is improved so as to have sensitivity higher than sensitivity of a circular dichroism fluorescent microscope 200' in accordance with Embodiment 2 and (ii) that is capable of analyzing a circularly polarized luminescence dichroism spectrum. For convenience of an explanation, members having the same functions as those described in Reference Embodiments 1 and 2 and Embodiments 1 and 2 are given the same reference numerals, and the explanations thereof are omitted. The present embodiment explains how the present embodiment is different from Reference embodiments 1 and 2 and Embodiments 1 and 2.

Figure 5:
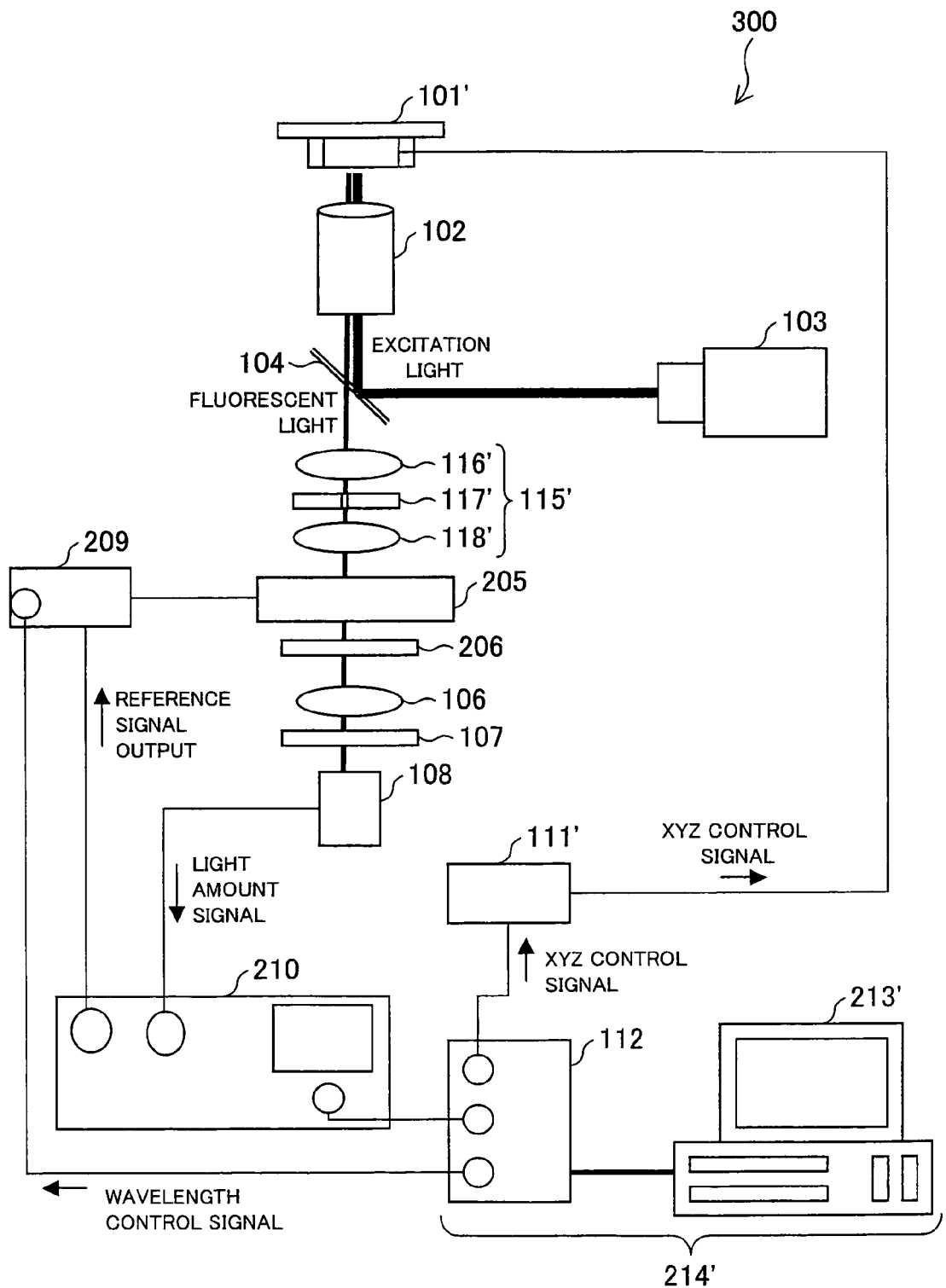
FIG. 5 is a diagram schematically illustrating another configuration of a circular dichroism fluorescent microscope of an embodiment in accordance with the present invention, which circular dichroism fluorescent microscope carries out three-dimensional analysis of a circularly polarized luminescence dichroism spectrum.

FIG. 5 is a diagram schematically illustrating a configuration of a circular dichroism fluorescent microscope 300 in accordance with the present embodiment. The circular dichroism fluorescent microscope 300 is a fluorescent microscope that three-dimensionally analyzes a circularly polarized luminescence dichroism (CPL) spectrum analysis of a sample by having a confocal microscope configuration.

Specifically, the circular dichroism fluorescent microscope 300 includes a sample stage 101', an optical lens 102, a light source 103, a wavelength selecting mirror 104, a circularly polarizing/modulating section 205, a polarization blocking section 206, an optical lens 106, a wavelength selecting section 107, a fluorescence measuring section 108, a polarization controlling section 209, a detection controlling section 210, a stage controlling section 111', a signal processing section 214', and a confocal section 115'.

As shown in FIG. 5, the circular dichroism fluorescent microscope 300 differs from the circular dichroism fluorescent microscope 200' only in that the confocal section 115' is disposed in a preceding section of the circularly polarizing/modulating section 205. Other than this point, the circular dichroism fluorescent microscope 300 has the same configuration as the circular dichroism fluorescent microscope 200' in accordance with Embodiment 2, and thus the explanations thereof are omitted.

Next, the following explains an operation of the circular dichroism fluorescent microscope 300. An operation of the circular dichroism fluorescent microscope 300 is basically the same as the operation of the circular dichroism fluorescent microscope 200', except in that fluorescence that is emitted from a sample passes through the confocal section 115' and then enters the circularly polarizing/modulating section 205. In this arrangement, the fluorescence that is emitted from the sample does not directly reach the circularly polarizing/modulating section 205 but passes through the confocal section 115' first. In this case, out of the fluorescence that is emitted from the sample, only light that focuses on a fine aperture section passes through the confocal section 105. Meanwhile, other light is blocked. The fluorescence is thus adjusted. Then, the adjusted fluorescence reaches the circularly polarizing/modulating section 205.

The inventors of the present invention found, through their own research, that data sensitivity obtained is remarkably improved by providing, as described above, in the preceding section of the circularly polarizing/modulating section 205, the confocal section 115' that has a fine aperture section and is for adjusting the fluorescence light that is emitted from the sample. That is, the inventors found an arrangement in which, with the use of the confocal section 115', the fluorescence light is converted to a parallel light beam (adjusted fluorescent light) and then enters the circularly polarizing/modulating section 205. Such finding is neither taught nor suggested in the Patent Document 3. Thus, this finding can be regarded as a technological idea unique to the present invention.

The following provides an explanation for helping the understanding of the feature of the present invention. In the explanation, the present invention is compared with the Patent Document 3 that discloses an invention similar to the present invention.

Specifically, as described above, an apparatus disclosed in the Patent Document 3 uses a semi-transmissive mirror as means for transmitting only an excitation light and reflecting a fluorescence light. Yet, a loss of intensity of the excitation light that enters the semi-transmissive mirror occurs, because the semi-transmissive mirror does not have a wavelength selectivity and is semi-transmissive. In addition, loss of intensity of the fluorescence light that is reflected occurs. Such losses significantly deteriorate measurement accuracy. Moreover, unless the semi-transmissive mirror is positioned exactly at 45 degrees with respect to a light path, distortion occurs. This results in significant deteriorations in measurement accuracy and measurement stability.

On the other hand, the present invention uses a wavelength selecting mirror instead of the semi-transmissive mirror. A wavelength selecting mirror reflects light (excitation light in the present invention) whose wavelength is short and allows light (fluorescence light in the present invention) whose wavelength is long to travel straight.

Therefore, the present invention technically differs from the invention disclosed in the Patent Document 3 to a large extent in whether a wavelength selecting mirror is used or a semi-transmissive mirror is used. The difference in the arrangements makes the present invention different from the invention disclosed in the Patent document 3 in (i) a light path of an excitation light (the excitation light is reflected in the present invention while the excitation light travels straight in the invention disclosed in the Patent Document 3) and (ii) a light path of fluorescent light (the fluorescent light travels straight in the present invention while the fluorescent light is reflected in the invention disclosed in the Patent Document 3).

Due to the difference in the arrangements, while amounts of intensity losses in the invention disclosed in the Patent Document 3 are significantly large (50% of the excitation light and 50% of the fluorescence light are lost), amounts of intensity losses in the present invention is small (5% of the excitation light and 10% of the fluorescence light are lost). Thus, the arrangement described above allows the present invention to reliably provide measurement stability.

Besides, an iris is disposed in the vicinity of a detecting section in an apparatus disclosed in the Patent Document 3. In this arrangement, the fluorescence light that is emitted from a sample is multi-reflected. This causes an error during detection of a circularly polarized light component. On the other hand, in the present invention, a confocal section 115' is provided between a wavelength selecting mirror 104 and a circularly polarizing/modulating section 205 (modulator). As a result, a non-parallel light beam component is removed. Thus, it becomes possible to carry out measurement with high sensitivity.

As described above, the fluorescence that is emitted from the sample is adjusted once, and then reaches the circularly polarizing/modulating section 205. This remarkably improves sensitivity of confocal data that is detected by the fluorescence detecting section 108. For example, as compared to the circular dichroism fluorescent microscope 200', the circular dichroism fluorescent microscope 300 has sensitivity and reproducibility that are improved by approximately ten times.

Therefore, with the use of the circular dichroism fluorescent microscope 300, it is possible to analyze, with high accuracy and high reproducibility, a sample that has a small circularly polarized light component, although the sample cannot be analyzed with the use of the circularly dichroism fluorescent microscope 200'.

Thus, in the circular dichroism fluorescent microscope in accordance with the present embodiment, it is preferable that a confocal section is disposed between the wavelength selecting mirror 104 and the fluorescence detecting section 108. Moreover, it is more preferable that the confocal section is disposed between the wavelength selecting mirror 104 and circular polarization/modulation means 205.

The present invention may also include a circular dichroism fluorescent microscope described below.

(a) A circular dichroism fluorescent microscope includes: a light source; circular polarization/modulation means to convert, into a right circularly polarized light and a left circularly polarized light, a light beam emitted from the light source; a first optical lens for focusing the right circularly polarized light and the left circularly polarized light on a sample and irradiating the sample with use of the right circularly polarized light and the left circularly polarized light, the right circularly polarized light and the left circularly polarized light having passed through the circular polarization/modulation means; a second optical lens for focusing fluorescence emitted from the sample; wavelength selection means to transmit, only fluorescence having a predetermined wavelength out of the fluorescence focused by the second optical lens; fluorescence measurement means to detect the fluorescence having passed through the wavelength selection means and convert the fluorescence detected into a fluorescence intensity signal; and signal processing means to calculate, based on the fluorescence intensity signal generated by the fluorescence measurement means, a difference between (i) an intensity of fluorescence emitted from the sample at the time when the sample is irradiated with use of the right circularly polarized light and (ii) an intensity of fluorescence emitted from the sample at the time when the sample is irradiated with use of the left circularly polarized light.

(b) The circular dichroism fluorescent microscope as set forth in (a), further includes: polarization control means to carry out control so that the circular polarization/modulation means converts, alternately into the right circularly polarized light and the left circularly polarized light at a predetermined modulation frequency, the light beam emitted from the light source; and detection control means to carry out control so that the signal processing means (1) extracts, in synchronization with the modulation frequency, an alternating-current component out of the fluorescence intensity signal generated by the fluorescence measurement means, and then (2) calculates the difference between (1') the intensity of the fluorescence emitted from the sample at the time when the sample is irradiated with the use of the right circularly polarized light and (2') the intensity of the fluorescence emitted from the sample at the time when the sample is irradiated with the use of the left circularly polarized light.

(c) The circular dichroism fluorescent microscope as set forth in (a), further includes: a third optical lens provided between the second optical lens and the wavelength selection means.

(d) The circular dichroism fluorescent microscope as set forth in (a), wherein: the first optical lens and the second optical lens are of a same optical lens.

(e) The circular dichroism fluorescent microscope as set forth in any one of (a) to (d) further includes confocal means provided between the second optical lens and the wavelength selection means.

(f) A circular dichroism fluorescent microscope includes: a light source; a first optical lens for focusing a light beam emitted from the light source and performing irradiation of the light beam focused; a second optical lens for focusing fluorescence emitted from a sample; circular polarization/modulation means to convert, into a right circularly polarized light and a left circularly polarized light, the fluorescence having passed through the second optical lens; polarized light block means to block, out of the right circularly polarized light and the left circularly polarized light, either a right circular polarized light component or a left circular polarized light component; wavelength selection means to transmit, out of the circularly polarized light components having passed through the polarized light block means, only light having a predetermined wavelength; fluorescence measurement means to detect the fluorescence that has passed through the wavelength selection means and convert the fluorescence into a florescence intensity signal; and signal processing means to calculate, based on the fluorescence intensity signal generated by the fluorescence measurement means, a difference between an intensity of the right circularly polarized light component and an intensity of the left circularly polarized light component of the fluorescence emitted from the sample.

(g) The circular dichroism fluorescent microscope as set forth in (f), further includes: polarization control means to carry out control so that the circular polarization/modulation means converts, alternately into the right circularly polarized light and the left circularly polarized light at a predetermined modulation frequency, the fluorescence having passed though the second optical lens; and detection control means to carry out control so that the signal processing means (1) extracts, in synchronization with the modulation frequency, an alternating-current component out of the fluorescence intensity signal generated by the fluorescence measurement means, and then (2) calculates the difference between the intensity of the right circularly polarized light component and the intensity of the left circularly polarized light component of the fluorescence emitted from the sample.

(h) The circular dichroism fluorescent microscope as set forth in (f) or (g), further includes: a third optical lens provided between the polarized light block means and the wavelength selection means.

(i) The circular dichroism fluorescent microscope as set forth in either (f) or (g), wherein: the first optical lens and the second optical lens are of a same optical lens.

(j) The circular dichroism fluorescent microscope as set forth in any one of (f) to (i) further including: confocal means provided between the circular polarization/modulation means and the polarized light block means or between the polarized light block means and the wavelength selection means.

(k) The circular dichroism fluorescent microscope as set forth in any one of (a) to (j), further includes; image processing means to form an image of the sample, based on information on the difference between the intensities of the fluorescence, the intensities being calculated by the signal processing means.

The arrangements described in Reference Embodiments and Embodiments are only examples of a circular dichroism fluorescent microscope of the present invention. It is obvious that the invention is not limited to thus described arrangements, but the embodiments and the arrangements may be varied in many ways in the scope that is reasonable according to the object of the present invention. A technological part that is not described in the above Reference Embodiments and Embodiments may suitably utilize as appropriate techniques in descriptions of other Reference Examples and Embodiments and/or techniques at the level of technology at the time of filing the present application. Furthermore, the arrangements described in Reference Embodiments and Embodiments may be applied in many variations, provided that such variations do not exceed the scope of the patent claims set forth below. A reference embodiment and an embodiment based on a proper combination of technical means disclosed in different reference embodiments and embodiments are encompassed in the technical scope of the present invention.

The blocks, in particular, a signal processing section, a polarization controlling section, a detection controlling section, and a stage controlling section (hereinafter, simply referred to as signal processing section and the like) of the circular dichroism fluorescent microscope may be constituted by hardware logic or may be realized by software by using a CPU in the following manner.

That is, the circular dichroism fluorescent microscope includes a CPU (central processing unit) that executes the order of a control program for realizing the aforesaid functions, ROM (read only memory) that stores the control program, RAM (random access memory) that develops the control program in an executable form, and a storage device (storage medium), such as memory, that stores the control program and various types of data therein. With this arrangement, the object of the present invention is realized by a predetermined storage medium. The storage medium stores, in a computer-readable manner, program codes (executable code program, intermediate code program, and source program) of the control program of the circular dichroism fluorescent microscope of the present invention, which is software for realizing the aforesaid functions. The storage medium is provided to the circular dichroism fluorescent microscope. With this arrangement, the circular dichroism fluorescent microscope (alternatively, CPU or MPU) as a computer reads out and executes program code stored in the storage medium provided.

The storage medium may be tape based, such as a magnetic tape or cassette tape; disc based, such as a magnetic disk including a floppy® disc and hard disk and optical disk including CD-ROM, MO, MD, DVD, and CD-R; card based, such as an IC card (including a memory card) and an optical card; or a semiconductor memory, such as a mask ROM, EPROM, EEPROM, and a flash ROM.

Further, the circular dichroism fluorescent microscope of the present invention may be arranged so as to be connectable to a communications network so that the program code is supplied to the microscope through the communications network. The communications network is not to be particularly limited. Examples of the communications network include the Internet, intranet, extranet, LAN, ISDN, VAN, CATV communications network, virtual private network, telephone network, mobile communications network, and satellite communications network. Further, a transmission medium that constitutes the communications network is not particularly limited. Examples of the transmission medium include (i) wired lines such as IEEE 1394, USB, power-line carrier, cable TV lines, telephone lines, and ADSL lines and (ii) wireless connections such as IrDA and remote control using infrared light, Bluetooth®, 802.11, HDR, mobile phone network, satellite connections, and terrestrial digital network. Note that the present invention can be also realized by the program codes in the form of a computer data signal embedded in a carrier wave which is embodied by electronic transmission.

INDUSTRIAL APPLICABILITY

A circular dichroism fluorescent microscope in accordance with the present invention provides an effect such that a spectrum of a fluorescence detected circular dichroism (FDCD) or that of a circularly polarized luminescence dichroism (CPL) can be analyzed by using a small amount of a sample. Thus, it is possible to analyze, (i) without a large amount of the sample and (ii) with high accuracy, chirality information of the sample. Therefore, the circular dichroism fluorescent microscope of the present invention makes it possible to analyze, directly in a cell, for example, chirality information, a high-order structure, a conformation, and the like of a biomolecule, such as protein and nucleic acid, present in the cell.

The circular dichroism fluorescent microscope in accordance with the present invention can analyze information on chirality and a high-order structure of a biomolecule and the like. Therefore, the circular dichroism fluorescent microscope is applicable not only in academic fields such as medical science, physiology, and the like but also in various industries such as a diagnosis/medical instrument industry, an analytical instrument industry, a pharmaceutical industry, a food industry, and the like.

The invention claimed is:

1. A circular dichroism fluorescent microscope, comprising:
    a light source;
    a circular polarization/modulation device to convert, into a right circularly polarized light and a left circularly polarized light, a light beam emitted from the light source;
    a first optical lens for focusing the right circularly polarized light and the left circularly polarized light on a sample and irradiating the sample with use of the right circularly polarized light and the left circularly polarized light, the right circularly polarized light and the left circularly polarized light having passed through the circular polarization/modulation device;
    a second optical lens for focusing fluorescence emitted from the sample;
    a wavelength selection device to transmit only fluorescence having a set wavelength out of the fluorescence focused by the second optical lens;
    a fluorescence measurement device to detect the fluorescence having passed through the wavelength selection device and converts the fluorescence detected into a fluorescence intensity signal;
    a signal processing device to calculate, based on the fluorescence intensity signal generated by the fluorescence measurement device, a difference between (i) an intensity of fluorescence emitted from the sample at the time when the sample is irradiated with use of the right circularly polarized light, and (ii) an intensity of fluorescence emitted from the sample at the time when the sample is irradiated with use of the left circularly polarized light;
    a confocal device provided between the second optical lens and the wavelength selection device, the confocal device having a fine aperture section;
    a wavelength selecting mirror provided between the second optical lens and the confocal device, the wavelength selecting mirror reflecting the right circularly polarized light and the left circularly polarized light that have passed through the circular polarization/modulation device while transmitting the fluorescence emitted from the sample,
    the first optical lens and the second optical lens being of a same optical lens; and
    a circular polarization and fluorescence detection wavelength control device (i) to control, by an external signal, the set wavelength of the wavelength selection device, and (ii) to control a modulation light wavelength of the circular polarization/modulation device.

2. The circular dichroism fluorescent microscope as set forth in claim 1, further comprising:
    a polarization control device to carry out control so that the circular polarization/modulation device converts, alternately into the right circularly polarized light and the left circularly polarized light at a set modulation frequency, the light beam emitted from the light source; and
    a detection control device to carry out control so that the signal processing device (i) extracts, in synchronization with the modulation frequency, an alternating-current component out of the fluorescence intensity signal generated by the fluorescence measurement device, and then (ii) calculates the difference between (a) the intensity of the fluorescence emitted from the sample at the time when the sample is irradiated with the use of the right circularly polarized light and (b) the intensity of the fluorescence emitted from the sample at the time when the sample is irradiated with the use of the left circularly polarized light.

3. The circular dichroism fluorescent microscope as set forth in claim 1, further comprising:
    a third optical lens provided between the second optical lens and the wavelength selection device.

4. The circular dichroism fluorescent microscope as set forth in claim 1, wherein:
    a diameter of the fine aperture section is in a range from more than or equal to 10 μm to less than or equal to 100 μm.

5. The circular dichroism fluorescent microscope as set forth in claim 1, further comprising:
    an image processing device to form an image of the sample, based on information on the difference between the intensities of the fluorescence, the intensities being calculated by the signal processing device.

6. A circular dichroism fluorescent microscope, comprising:
    a light source;
    a first optical lens for focusing a light beam emitted from the light source and performing irradiation of the light beam focused;
    a second optical lens for focusing fluorescence emitted from a sample;
    a wavelength selecting mirror for reflecting an excitation light from the light source while transmitting the fluorescence emitted from the sample;
    a circular polarization/modulation device to convert, into linearly polarized light components, a right circularly polarized light component and a left circularly polarized light component of the fluorescence having passed through the second optical lens;

a polarized light blocking device to block, out of the linearly polarized light components, either a vertical linearly polarized light component or a horizontal linearly polarized light component;

a wavelength selection device to transmit, out of the circularly polarized light components having passed through the polarized light blocking device, only light having a set wavelength;

a fluorescence measurement device to detect the fluorescence that has passed through the wavelength selection device and convert the fluorescence into a florescence intensity signal;

a signal processing device to calculate, based on the fluorescence intensity signal generated by the fluorescence measurement device, a difference between an intensity of the right circularly polarized light component and an intensity of the left circularly polarized light component of the fluorescence emitted from the sample;

a confocal device provided between the wavelength selecting mirror and the fluorescence measurement device, the confocal device having a fine aperture section; and a circular polarization and fluorescence detection wavelength control device (i) to control, by an external signal, the set wavelength of the wavelength selection device, and (ii) to control a modulation light wavelength of the circular polarization/modulation device.

7. The circular dichroism fluorescent microscope as set forth in claim 6, wherein:

the confocal device is provided between the wavelength selecting mirror and the circular polarization/modulation device.

8. The circular dichroism fluorescent microscope as set forth in claim 6, wherein:

the confocal device has a function for adjusting the fluorescence that is to reach the circular polarization/modulation device.

9. The circular dichroism fluorescent microscope as set forth in claim 6, further comprising:

a polarization control device to carry out control so that the circular polarization/modulation device converts, alternately into the right circularly polarized light and the left circularly polarized light at a set modulation frequency, the fluorescence having passed though the second optical lens; and a detection control device to carry out control so that the signal processing device (i) extracts, in synchronization with the modulation frequency, an alternating-current component out of the fluorescence intensity signal generated by the fluorescence measurement device, and then (ii) calculates the difference between the intensity of the right circularly polarized light component and the intensity of the left circularly polarized light component of the fluorescence emitted from the sample.

10. The circular dichroism fluorescent microscope as set forth in claim 6, further comprising:

a third optical lens provided between the polarized light block device and the wavelength selection device.

11. The circular dichroism fluorescent microscope as set forth in claim 6, wherein:

the first optical lens and the second optical lens are of a same optical lens.

12. The circular dichroism fluorescent microscope as set forth in claim 6, wherein:

a diameter of the fine aperture section is in a range from more than or equal to 10 μm to less than or equal to 100 μm.

13. The circular dichroism fluorescent microscope as set forth in claim 6, further comprising;

an image processing device to form an image of the sample, based on information on the difference between the intensities of the fluorescence, the intensities being calculated by the signal processing device.

* * * * *